United States Patent [19]

Hirsch

[11] Patent Number: 5,001,117

[45] Date of Patent: Mar. 19, 1991

[54] USE OF LECITHIN TO RESTORE OLFACTION AND TASTE

[75] Inventor: Alan R. Hirsch, Chicago, Ill.

[73] Assignee: Pharmacaps, Inc., Elizabeth, N.J.

[21] Appl. No.: 319,744

[22] Filed: Mar. 7, 1989

[51] Int. Cl.⁵ .......................................... A61K 31/685
[52] U.S. Cl. ....................................................... 514/78
[58] Field of Search ............................................ 514/78

[56] References Cited

U.S. PATENT DOCUMENTS

| | | | |
|---|---|---|---|
| 4,221,784 | 9/1980 | Growdon et al. | 424/199 |
| 4,366,145 | 12/1982 | Stoopak et al. | 424/37 |
| 4,486,412 | 12/1984 | Shah et al. | 424/156 |
| 4,626,527 | 12/1986 | Wurtman et al. | 514/78 |
| 4,708,834 | 11/1987 | Cohen et al. | 264/4.3 |

OTHER PUBLICATIONS

N. Halasz, *Neuroscience* 10: 579–619 (1983).
Skouby, *Acta Physiol. Scand.* 32: 252–258 (1954).
J. K. Blusztajn and R. J. Wurtman, *Science*, 221, 614–620 (1983).
M. M. Esiri and G. K. Wilcock, *J. Neurol. Neurosurg. and Psychiatry*, 47, 56–60 (1984).
"Food for Thought", Advanced Nutritional Technology, Inc., Elizabeth, N.J. (1986).
A. J. Gelenberg et al., *Am. J. Psychiatry*, 136, 772–776 (1979).
I. V. Jackson et al., *Am. J. Psychiatry*, 136, 1458–1460 (1979).
"Lechithin (phosphatidylcholine) and Its Uses", Advanced Nutritional Technology, Inc., Elizabeth, N.J. (1986).
A. Little et al., *J. Neurol. Neurosurg. and Psychiatry*, 48, 736–742 (1985).
I. Lopez and I. R. Berry, "Plasma Choline Levels in Humans After Oral Administration of Highly Purified Phosphatidylcholine (PC) in Capsules", in *Alzheimer's Disease: Advances in Basic Research and Therapies*, R. J. Wurtman et al., eds., Raven Press, New York (1987) at 467–470.
R. F. Mervis et al., "Chronic Dietary Choline and Phosphatidylcholine Induces Dendritic Growth in Pyramidal Cells of Aging Mouse Neocortex", in *Alzheimer's Disease: Advances in Basic Research and Therapies*, R. J. Wurtman et al., eds., Raven Press, New York (1987).
"Physician's Product Information", Advanced Nutritional Technology, Inc., Elizabeth, N.J. (1988).
M. Serby, *Olfaction and Neuropsychiatry* (Abstract distributed at a lecture given by Dr. Serby at the Institute for Research in Behavioral Neurosciences, Dec. 12, 1987).
M. Serby et al., Letter entitled "Olfaction in Dementia", *J. Neurol. Neurosurg. and Psychiatry*, 848–849 (1985).
Sigma Chemical Company, *Biochemicals Organic Compounds*, 1184–1185 (1989).
M. D. Warner et al., *Biol. Psychiatry*, 21, 116–118 (1986).
"Why Use PhosChol ®?", Advanced Nutritional Technology, Inc., Elizabeth, N.J. (1986).
J. L. Wood and R. G. Allison, *Effects of Consumption of Choline and Lecithin on Neurological and Cardiovascular Systems*, Life Sciences Research Office, Federation of American Societies for Experimental Biology, Bethesda, Md., (1981).
R. J. Wurtman and S. H. Zeisel, in *Alzheimer's Disease: A Report of Progress*, S. Corkin et al., eds., Raven Press, N.Y. (1982).
R. J. Wurtman et al., *Pharmacological Reviews*, 32, 315–335 (1981).

*Primary Examiner*—Douglas W. Robinson
*Assistant Examiner*—Raymond J. Henley
*Attorney, Agent, or Firm*—Merchant, Gould, Smith, Edell, Welter & Schmidt

[57] ABSTRACT

A method is provided to treat hyposmia or anosmia by administering an effective amount of a choline-containing compound to a patient afflicted with said conditions.

5 Claims, No Drawings

USE OF LECITHIN TO RESTORE OLFACTION AND TASTE

BACKGROUND OF THE INVENTION

Pure lecithin is also referred to as L-α-lecithin or L-α-phosphatidylcholine (PC). This compound has the general formula $(R_1CO_2CH_2-)R_2CO_2CH(-CH_2OPO_2^--OCH_2CH_2N(CH_3)_3^+)$, wherein the groups $R_1CO_2-$ and $R_2CO_2-$ are derived from one or more fatty acids such as stearic, oleic, palmitic, palmitoleic, linoleic, linoledonic acid and arachidonic acid. Naturally-occurring lecithin, derived from sources such as bovine organs, egg yolk or soybeans, provides most of the choline that is present in the diet, and its consumption raises blood choline levels The average dietary intake of PC has been estimated to be 2.6-5.8 g/day. Therefore, if the average person consumes 8-10 g of pure PC, blood choline levels will about double.

After PC is consumed, half of it is rapidly broken down within the intestines to yield choline, which enters the blood stream. The other half is absorbed into the lymph without being degraded; it aids in metabolizing cholesterol and other fats, and eventually some of its choline content enters the bloodstream.

Choline itself is rarely ingested because most foods contain choline in the form of PC. Administration of choline salts, rather than PC, is an inefficient way to increase blood choline levels because most of the free choline is destroyed by bacteria in the intestines. Furthermore, this bacterial action provides amines, which give the body an unpleasant odor of rotten fish. Therefore, the administration of PC is the preferred way to raise blood choline levels. Choline circulating in the blood after PC ingestion is taken up into all cells of the body. The brain has a unique way of ensuring that its nerve cells will receive adequate supplies of circulating choline. A protein molecule within the brain's capillaries traps the circulating choline, and then transports it across the blood-brain barrier, into the brain. Once in the brain, choline is incorporated into the brain's own PC, which is an essential and major part of neuronal membranes. See J. K. Blusztajn et al., *Science*, 221, 614 (1983). Circulating choline transported into the brain has an additional function for a special group of nerve cells that make acetylcholine, which is released into synapses as a neurotransmitter. The choline provides the essential precursor used to synthesize acetylcholine (R. J. Wurtman et al., in *Alzheimer's Disease: A Report of Progress in Research*, S. Corkin et al., eds., Raven Press, NY (1982)). In the absence of adequate choline, the ability of these nerve cells to transmit messages to other cells across synapses is impaired. In contrast, when supplemental choline is provided, these messages can be amplified. These findings, based upon studies in experimental animals, isolated organs, and cultured cells, provide the scientific basis for using PC supplements to increase acetylcholine release, especially in clinical conditions and disorders where cholinergic tone is impaired (R. J. Wurtman et al., *Pharma-col. Rev.*, 32, 315 (1981)). Thus, PC's ability to increase blood choline, brain choline, and brain acetylcholine levels has led to its use as a supplement for patients with brain diseases associated with impaired acetylcholine neurotransmission, such as tardive dyskinesia (TD). Similarly, PC's central role in the composition and functional properties of neuronal membranes suggests its utility as a supplement for patients with brain diseases associated with the dissolution of neuronal membranes, such as Alzheimer's disease. The utility of PC (and choline) as a nutritional supplement is best documented in TD, although it has been tested in patients with a variety of brain diseases, including Alzheimer's disease, Huntington's disease, Gilles de la Tourette syndrome, familial ataxia, myasthenia gravis, epilepsy, and mania. J. H. Growdin et al. (U.S. Pat. No. 4,221,784) disclose the use of lecithin to alleviate the effects of TD, manic-depressive disease, memory impairment and familial ataxia I. V. Jackson et al., in *Am. J. Psychiatry*, 136, 11 (1979) reported a significant improvement in six patients with moderate or severe TD who were given 50 g/day of lecithin for two weeks. A. Little et al., *J. Neurology*, 48, 736 (1985) reported that administration of 20-25 g of purified soya lecithin to Alzheimer's disease patients for six months improved the performance in an older subgroup of patients who had been identified as "poor compliers."

In order for olfaction (the sense of smell) to occur, the odoriferous chemicals must move through the nose to the olfactory receptors and then through the olfactory nerve to the olfactory bulb. The signal of the smell then progresses through the olfactory bulb to the brain. Acetylcholine is present in the olfactory bulb, and nasal administration of acetylcholine has been reported to lead to increased olfactory acuity. Furthermore, the anesthetic scopolamine lowers acetylcholine levels and has been reported to decrease olfactory detection in normal subjects. More than 200,000 patient visits to physicians occur each year because of complaints relating to smell and/or taste. Approximately four million Americans have abnormalities in their ability to smell or taste, and more than 90% of these patients have abnormalities in the sense of smell.

Therefore, a need exists for a method to reverse hyposmia (decreased sense of taste and smell) or anosmia (absence of sense of taste and smell), without deleterious side effects.

BRIEF DESCRIPTION OF THE INVENTION

The present invention provides a method to reverse hyposmia (reduction in ability to taste and smell) or anosmia (total loss of ability to taste and smell) in human patients afflicted with these conditions comprising the administration to said patients of an effective amount of a choline-containing compound, such as lecithin. Other choline-containing compounds include nontoxic choline salts such as choline chloride, choline dihydrogen citrate and choline bitartrate, as well as lysophosphatidylcholine and dilysophosphatidyl choline. The choline-containing compound can be administered to said patients orally, in amounts effective to substantially increase blood choline levels, without substantial deleterious side effects such as nausea or increased salivation.

Although it is possible that the increased blood choline levels improve the functioning of the olfactory bulb, the olfactory tubercle or the olfactory lobe of the brain via increasing the amount or activity of acetylcholine in these organs or in other parts of the olfactory chain, the mechanism of this effect is unknown.

As used herein, the term "lecithin" includes pure (≦99%) phosphatidylcholine (PC), as well as commercially-available grades of lecithin which contain lesser amounts of PC, e.g., from about 90-95% PC to as little as 10-15% PC, in combination with other phosphatides which do not contain choline. Pure phosphatidylcholine is commercially available, as are a number of grades of "lecithin" which contain less PC. (See Sigma Chemical Co., catalog of *Biochemical-Organic Compounds* (1989) at pages 1184–1185). However, high-PC lecithin is preferred for use in the present method, since PC is believed to be the active ingredient in lecithin, and since it reduces the volume of the compound which must be ingested by the patient to achieve the desired effect. Also, administration of purified PC is more efficacious, since the non-choline containing phosphatides can compete for in vivo absorption of PC following administration.

DETAILED DESCRIPTION OF THE INVENTION

In the practice of the present invention, it is preferred to administer the choline-containing compound such as lecithin in combination with a pharmaceutically-acceptable carrier, e.g., lecithin can be included in a tablet, capsule, or in a liquid carrier so that the dosage form contains about 50–90% wt-% PC. Preferably, lecithin is dissolved or dispersed in a semi-liquid or liquid fill material and encapsulated in soft gelatin. For examples of these unit dosage forms, see U.S. Pat. Nos. 4,486,412; 4,708,834, and 4,366,145, the disclosures of which are incorporated by reference herein. Administration of lecithin in soft gelatin capsules in a liquid or semi-liquid vehicle is preferred since such encapsulated dosage forms are easy to swallow, protect the PC from degradation or contamination, provide a precisely measured amount of PC, and can increase the bioavailability of the PC. Unit dosage forms which provide 900 mg, 565 mg or 200 mg of pure PC encapsulated in a liquid vehicle in soft gelatin are commercially available under the trademark PhosChol® from Advanced Nutritional Technology, Inc., Elizabeth, NJ; as PhosChol® 900, PhosChol® 565, and PhosChol® 200, respectively.

Lecithin can also be orally administered in liquid form, e.g., as a thickened, sweetened aqueous or oily emulsion, or in granular form, e.g., in hard gelatin capsules. A commercially-available liquid form of lecithin is available from Nutritional Technology, Inc. as PhosChol® concentrate, which contains about 60 wt-% PC in an oil vehicle.

Although oral administration is effective and is preferred, parenteral administration of lecithin in combination with a suitable liquid vehicle, can be employed to treat patients who cannot swallow or otherwise ingest orally.

Blood level studies utilizing PhosChol® 900 have demonstrated that a total daily oral dose of about 3 g of pure PC (3–4 900 mg PC capsules) will raise blood choline levels by 50%, e.g., from about 8 nm/mg choline to about 12 nm/mg choline. A daily dose of about 9 g of PC (ten 900 mg capsules) will double blood choline levels (from about 8 nm/mg to about 16 nm/mg). Plasma levels as high as 25 nm/mg can be achieved using, e.g., one 9 g dose at 0 hours and one 9 g dose at 4 hours. Plasma levels of up to about 50 nm/ml can be attained in accord with the present method and doses of up to 50–100 g/day of PC can be administered without undue side effects for extended periods of time. See I. V. Jackson et al., *Am. J. Psychiatry*, 136, 1458 (1979); and Federation of American Societies for Experimental Biology, report prepared for Food and Drug Administration, Bureau of Foods (1981), "Effects of Consumption of Choline and Lecithin on Neurological and Cardiovascular Systems," Life Sciences Research Office, Bethesda, MD, USA.

A course of treatment can comprise an amount of lecithin effective to provide about 5–25 g of PC/day for at least about one month. However, effective amounts of lecithin can be administered indefinitely, as required by the patient and directed by the physician.

The invention will be described further by reference to the following Example.

EXAMPLE

Ten patients were selected for treatment, all of whom had complained of either hyposmia or anosmia for at least one year. All patients had been unsuccessfully treated by at least one other physician prior to entry into this study. The hyposmia or anosmia was confirmed and was demonstrated by a series of standard pre-screen tests to be unrelated to otherwise identifiable, treatable factors, such as B-12 deficiency. The screening tests include olfactory threshold tests, olfactory suprathreshold tests, gustatory threshold tests, gustatory suprathreshold tests, neurological examination, psychological testing, and electrical brain testing.

All patients received 9 g of PC/day (as PhosChol® concentrate) which was administered in a single dose, for 1–3 months. This amount would be expected to about double their serum choline concentration. Of the ten patients, four patients subjectively reported an improved ability to taste and smell.

The invention has been described with reference to various specific and preferred embodiments and techniques. However, it should be understood that many variations and modifications may be made while remaining within the spirit and scope of the invention.

What is claimed is:

1. A therapeutic method for reversing hyposmia or anosmia in a human patient in need thereof comprising orally administering to said patient an amount of a phosphatidylcholine effective to increase pretreatment blood choline levels to reverse hyposmia or anosmia.

2. The method of claim 1 wherein the amount of phosphatidylcholine is effective to at least double the pretreatment plasma choline levels of the patient.

3. The method of claim 1 wherein the phosphatidylcholine is administered in combination with a pharmaceutically-acceptable carrier.

4. The method of claim 3 wherein the carrier is a liquid.

5. The method of claim 4 wherein the phosphatidylcholine is administered in a liquid vehicle enclosed in a soft gelatin capsule.

* * * * *

UNITED STATES PATENT AND TRADEMARK OFFICE
CERTIFICATE OF CORRECTION

PATENT NO. : 5,001,117
DATED : March 19, 1991
INVENTOR(S) : Alan R. Hirsch

It is certified that error appears in the above-identified patent and that said Letters Patent is hereby corrected as shown below:

Column 2, Line 65, for "($\leq 99\%$)" read --($\geq 99\%$)--.

Signed and Sealed this

Fifteenth Day of September, 1992

Attest:

DOUGLAS B. COMER

*Attesting Officer*      *Acting Commissioner of Patents and Trademarks*